(12) United States Patent
Ulrich

(10) Patent No.: US 7,468,377 B2
(45) Date of Patent: *Dec. 23, 2008

(54) IMIDAZOPYRIDINE-DERIVATIVES AS INDUCTIBLE NO-SYNTHASE INHIBITORS

(75) Inventor: Wolf-Ruediger Ulrich, Constance (DE)

(73) Assignee: Altana Pharma AG, Constance (DE)

( * ) Notice: Subject to any disclaimer, the term of this patent is extended or adjusted under 35 U.S.C. 154(b) by 298 days.

This patent is subject to a terminal disclaimer.

(21) Appl. No.: 10/573,484

(22) PCT Filed: Sep. 30, 2004

(86) PCT No.: PCT/EP2004/052378

§ 371 (c)(1),
(2), (4) Date: Mar. 24, 2006

(87) PCT Pub. No.: WO2005/030771

PCT Pub. Date: Apr. 7, 2005

(65) Prior Publication Data

US 2007/0043073 A1 Feb. 22, 2007

(30) Foreign Application Priority Data

Oct. 1, 2003 (EP) ................................. 03022053

(51) Int. Cl.
*A01N 43/42* (2006.01)
*A61K 31/44* (2006.01)
*C07D 471/02* (2006.01)
*C07D 491/02* (2006.01)
*C07D 498/02* (2006.01)
*C07D 513/02* (2006.01)
*C07D 515/02* (2006.01)

(52) U.S. Cl. ...................................... 514/303; 546/118
(58) Field of Classification Search ................. 514/303; 546/126, 118
See application file for complete search history.

(56) References Cited

U.S. PATENT DOCUMENTS

| 4,045,564 | A | 8/1977 | Berntsson et al. | |
|---|---|---|---|---|
| 7,138,399 | B2 | 11/2006 | Ulrich | |
| 7,279,484 | B2 * | 10/2007 | Yamada et al. | 514/264.11 |

FOREIGN PATENT DOCUMENTS

| DE | 25 04 252 C2 | 8/1975 |
|---|---|---|
| EP | 0 125 756 A2 | 11/1984 |
| WO | 97/25030 A1 | 7/1997 |
| WO | 00/49015 A1 | 8/2000 |
| WO | 03/080607 A1 | 10/2003 |
| WO | 2005/030768 A1 | 4/2005 |
| WO | 2005/030769 A1 | 4/2005 |
| WO | 2005/030770 A1 | 4/2005 |
| WO | 2005/061496 A1 | 7/2005 |

OTHER PUBLICATIONS

Dugas et al., Cytokine, Vol. 15, 2001, pp. 96-107.*
Hua, L.L., et al., "Role of mitogen-activated protein kinases in inducible nitric oxide synthase and TNFα expression in human fetal astrocytes", *Journal of Neuroimmunology*, Vol. 126, pp. 180-189, (2002).
Kim, M-S, et al., "Water-soluble chitosan inhibits the production of pro-inflammatory cytokine in human astrocytoma cells activated by amyloid β peptide and interleukin-1β", *Neuroscience Letters*, Vol. 321, pp. 105-109, (2002).
D'Agostino, P., et al., "Tetracycline inhibits the nitric oxide synthase activity induced by endotoxin in cultured murine macrophages", *European Journal of Pharmacology*, Vol. 346, pp. 283-290, (1998).
Kiss, J., et al., "Time-dependent actions of nitric oxide synthase inhibition on colonic inflammation induced by trinitrobenzene sulphonic acid in rats", *European Journal of Pharmacology*, Vol. 336, pp. 219-224, (1997).
Sautebin, L., "Prostaglandins and nitric oxide as molecular targets for anti-inflammatory therapy", *Fitoterapia*, Vol. 71, pp. S48-S57, (2000).
Ohtsuka, M., et al., "PPA250 [3-(2,4-Difluorophenyl)-6-{2-[4-(1H-imidazol-1-ylmethyl)Phenoxy]ethoxy}-2-phenylpyridine], a Novel Orally Efffective Inhibitor of the Dimerization of Inducible Nitric-Oxide Synthase, Exhibits an Anti-Inflammatory Effect in Animal Models of Chronic Arthritis", *The Journal of Pharmacology and Experimental Therapeutics*, Vol. 33, No. 1, pp. 52-57, (2002).
Hansel, T. T., et al., "A selective inhibitor of inducible nitric oxide synthase inhibits exhaled breath nitric oxide in healthy volunteers and asthmatics", *FASEB J*, Vol. 17, pp. 1298-1300, (2003).
Tinker, A. C., et al., "1,2-Dihydro-4-quinazolinamines: Potent, Highly Selective Inhibitors of Inducible Nitric Oxide Synthase Which Show Antiinflammatory Activity in Vivo", *J. Med. Chem.*, Vol. 46, pp. 913-916, (2003).

(Continued)

*Primary Examiner*—D. Margaret Seaman
*Assistant Examiner*—Niloofar Rahmani
(74) *Attorney, Agent, or Firm*—The Nath Law Group; Joshua B. Goldberg; Sheldon M. McGee

(57) ABSTRACT

The compounds of Formula (I)

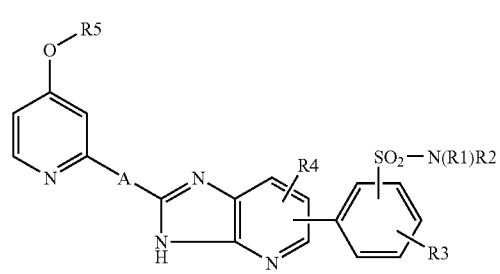

in which R1, R2, R3, R4, R5 and A have the meanings as given in the description are novel effective iNOS inhibitors.

9 Claims, No Drawings

OTHER PUBLICATIONS

Kankuri, E., et al., "Suppression of Acute Experimental Colitis by a Highly Selective Inducible Nitric-Oxide Synthase Inhibitor, N-[3-(Aminomethyl)benzyl]acetamidine", *The Journal of Pharmacology and Experimental Therapeutics,* Vol. 298, No. 3, pp. 1128-1132, (2001).

Liu, Z-Q, et al., "Specificity of inducible nitric-oxide synthase inhibitors: prospects for their clinical therapy", *Acta Pharmacol Sin,* Vol. 20, No. 11, pp. 1052-1056, (1999).

Salvemini, D., et al., "Dual Inhibition of Nitric Oxide and Prostaglandin Production Contributes to the Antiinflammatory Properties of Nitric Oxide Synthase Inhibitors", *J. Clin. Invest.,* Vol. 96, pp. 301-308, (1995).

Cuzzocrea, S., et al., "Beneficial effects of GW274150, a novel, potent and selective inhibitor of INOS activity, in a rodent model of collagen-induced arthritis", *European Journal of Pharmacology,* Vol. 453, pp. 119-129, (2002).

* cited by examiner

IMIDAZOPYRIDINE-DERIVATIVES AS INDUCTIBLE NO-SYNTHASE INHIBITORS

This application was filed under 35 U.S.C. 371 as a national stage of PCT/EP2004/052378, filed Sep. 30, 2004.

FIELD OF APPLICATION OF THE INVENTION

The invention relates to novel imidazopyridine derivatives, which are used in the pharmaceutical industry for the production of pharmaceutical compositions.

KNOWN TECHNICAL BACKGROUND

In the German Patent Application DE 2504252 and in the European Patent Application EP 0125756 3H-imidazo[4,5b]pyridine derivatives with anti-ulcer activity are described.

The International Application WO 0049015 describes pyridine compounds with inhibitory activity on the production of nitric oxide.

The International Application WO 0380607 describes alkoxypyridine derivatives with iNOS inhibitory activity.

DESCRIPTION OF THE INVENTION

It has now been found that certain novel, purposively selected aminosulfonylphenyl-substituted imidazopyridine derivatives, which are described in greater details below, differ profoundly from previously individualized compounds and have surprising and particularly advantageous and desired properties.

The invention thus relates to compounds of formula I

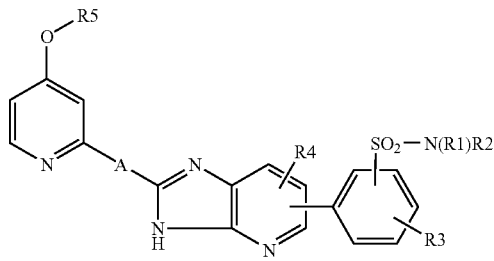

(I)

in which
R1 is hydrogen or 1-4C-alkyl,
R2 is hydrogen or 1-4C-alkyl,
R3 is hydrogen or halogen,
R4 is hydrogen, halogen, 1-4C-alkyl or 1-4C-alkoxy,
R5 is 1-4C-alkyl,
A is 1-4C-alkylene, and the salts, N-oxides and the salts of the N-oxides of these compounds.

1-4C-Alkyl is a straight-chain or branched alkyl radical having 1 to 4 carbon atoms. Examples are the butyl, isobutyl, sec-butyl, tert-butyl, propyl, isopropyl, and, particularly, the ethyl and methyl radicals.

1-4C-Alkoxy is a radical which, in addition to the oxygen atom, contains a straight-chain or branched alkyl radical having I to 4 carbon atoms. Alkoxy radicals having 1 to 4 carbon atoms which may be mentioned in this context are, for example, the butoxy, isobutoxy, sec-butoxy, tert-butoxy, propoxy, isopropoxy, and, particularly, the ethoxy and methoxy radicals.

1-4C-Alkylene is a straight chain alkylene radical having 1 to 4 carbon atoms. Examples which may be mentioned in this context are the methylene (—$CH_2$—), ethylene (—$CH_2$—$CH_2$—), trimethylene (—$CH_2$—$CH_2$—$CH_2$—) and the tetramethylene (—$CH_2$—$CH_2$—$CH_2$—$CH_2$—) radical.

Halogen stands for chlorine or fluorine.

N-oxide denotes the N-oxide on the pyridine which is substituted by the —O—R5 radical.

Suitable salts for compounds according to the invention—depending on substitution—are all acid addition salts or all salts with bases. Particular mention may be made of the pharmacologically tolerable inorganic and organic adds and bases customarily used in pharmacy. Those suitable are, on the one hand, water-insoluble and, particularly, water-soluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are—depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds according to the invention on an industrial scale, are converted into pharmacologically tolerable salts by processes known to the person skilled in the art.

According to expert's knowledge the compounds of the invention as well as their salts may contain, e.g. when isolated in crystalline form, varying amounts of solvents. Included within the scope of the invention are therefore all solvates and in particular all hydrates of the compounds according to this invention as well as all solvates and in particular all hydrates of the salts of the compounds according to this invention.

A person skilled in the art knows on the base of his/her expert knowledge that the compounds according to this invention can exist, with regard to the fused imidazo ring of the imidazopyridine system, in different tautomeric forms such as e.g. in the 1-H form or, preferably, in the 3-H form, which is shown in formula I. The invention includes all conceivable tautomers in pure form as well as in any mixing ratio. Particularly the present invention includes the pure 1-H— and, preferably, 3-H-tautomers as well as any mixtures thereof.

An embodiment of the compounds of the present invention include those compounds of formula I in which R5 is methyl.

Another embodiment of the compounds of the present invention include those compounds of formula I in which A is ethylene.

Another embodiment of the compounds of the present invention include those compounds of formula I in which R4 is hydrogen.

Another embodiment of the compounds of the present invention include those compounds of formula I in which R5 is methyl and A is ethylene.

Another embodiment of the compounds of the present invention include those compounds of formula I in which R4 is hydrogen, R5 is methyl and A is ethylene.

Another embodiment of the compounds of the present invention include those compounds of formula I in which the aminosulphonyl substituted phenyl moiety is bonded to the 6-position of the imidazopyridine ring.

The substituent R3 and the aminosulphonyl radical of compounds according to this invention can be attached in the ortho, meta or para position with respect to the binding position in which the phenyl ring is bonded to the imidazopyridine ring system, whereby in an embodiment of the present invention the aminosulphonyl radical is attached in the para position.

In this context, another embodiment of the compounds of the present invention include those compounds of formula I in which R3 is attached in the meta position and the aminosulphonyl radical is attached in the para position with respect to the binding position in which the phenyl ring is bonded to the imidazopyridine ring system.

Another special embodiment of the compounds of the present invention include those compounds which have one of the formulae Ia, Ib or Ic as shown below.

Compounds according to this invention worthy to be mentioned are those compounds of formula I, in which
R1 is hydrogen or 1-4C-alkyl,
R2 is hydrogen or 1-4C-alkyl,
R3 is hydrogen or halogen,
R4 is hydrogen,
R5 is methyl,
A is ethylene, and the salts, N-oxides and the salts of the N-oxides of these compounds.

Compounds according to this invention more worthy to be mentioned are those compounds of formula I, in which
R1 is hydrogen, methyl or ethyl,
R2 is hydrogen, methyl or ethyl,
R3 is hydrogen, chlorine or fluorine,
R4 is hydrogen,
R5 is methyl,
A is ethylene, and the salts, N-oxides and the salts of the N-oxides of these compounds.

Compounds according to this invention in particular worthy to be mentioned are those compounds of formula I, in which
R1 is hydrogen, methyl or ethyl,
R2 is hydrogen, methyl or ethyl,
R3 is hydrogen or fluorine,
R4 is hydrogen,
R5 is methyl,
A is ethylene, and the salts, N-oxides and the salts of the N-oxides of these compounds.

Compounds according to this invention in more particular worthy to be mentioned are those compounds of formula I, in which either
R1 is methyl,
R2 is methyl, and
R3 is fluorine, or
R1 is hydrogen, methyl or ethyl,
R2 is hydrogen, methyl or ethyl, and
R3 is hydrogen,
R4 is hydrogen,
R5 is methyl,
A is ethylene, and the salts, N-oxides and the salts of the N-oxides of these compounds.

An embodiment (embodiment a) worthy to be mentioned of this invention include compounds of formula Ia

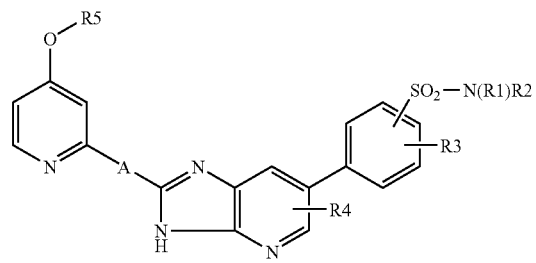

(Ia)

in which
R1 is hydrogen or 1-4C-alkyl,
R2 is hydrogen or 1-4C-alkyl,
R3 is hydrogen or halogen,
R4 is hydrogen,
R5 is 1-4C-alkyl,
A is 1-4C-alkylene, and the salts, N-oxides and the salts of the N-oxides of these compounds.

Compounds according to embodiment a worthy to be mentioned are those compounds of formula Ia, in which
R1 is hydrogen or 1-4C-alkyl,
R2 is hydrogen or 1-4C-alkyl,
R3 is hydrogen or halogen,
R4 is hydrogen,
R5 is methyl,
A is ethylene, and the salts, N-oxides and the salts of the N-oxides of these compounds.

Compounds according to embodiment a more worthy to be mentioned are those compounds of formula Ia, in which
R1 is hydrogen, methyl or ethyl,
R2 is hydrogen, methyl or ethyl,
R3 is hydrogen, chlorine or fluorine,
R4 is hydrogen,
R5 is methyl,
A is ethylene, and the salts, N-oxides and the salts of the N-oxides of these compounds.

Compounds according to embodiment a in particular worthy to be mentioned are those compounds of formula Ia, in which
R1 is hydrogen, methyl or ethyl,
R2 is hydrogen, methyl or ethyl,
R3 is hydrogen or fluorine,
R4 is hydrogen,
R5 is methyl,
A is ethylene, and the salts, N-oxides and the salts of the N-oxides of these compounds.

Compounds according to embodiment a in more particular worthy to be mentioned are those compounds of formula Ia, in which either
R1 is methyl,
R2 is methyl, and
R3 is fluorine, or
R1 is hydrogen, methyl or ethyl,
R2 is hydrogen, methyl or ethyl, and
R3 is hydrogen,
R4 is hydrogen,
R5 is methyl,
A is ethylene, and the salts, N-oxides and the salts of the N-oxides of these compounds.

A preferred embodiment (embodiment b) of this invention include compounds of formula Ib

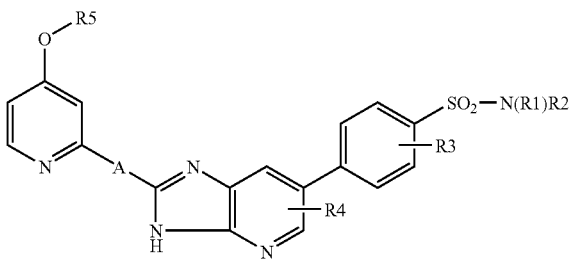

(Ib)

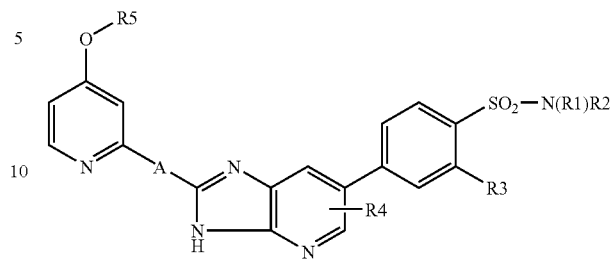

(Ic)

in which
R1 is hydrogen or 1-4C-alkyl,
R2 is hydrogen or 1-4C-alkyl,
R3 is hydrogen or halogen,
R4 is hydrogen,
R5 is methyl,
A is ethylene, and the salts, N-oxides and the salts of the N-oxides of these compounds.

Compounds according to embodiment b more worthy to be mentioned are those compounds of formula Ib, in which
R1 is hydrogen, methyl or ethyl,
R2 is hydrogen, methyl or ethyl,
R3 is hydrogen, chlorine or fluorine,
R4 is hydrogen,
R5 is methyl,
A is ethylene, and the salts, N-oxides and the salts of the N-oxides of these compounds.

Compounds according to embodiment b in particular worthy to be mentioned are those compounds of formula Ib, in which
R1 is hydrogen, methyl or ethyl,
R2 is hydrogen, methyl or ethyl,
R3 is hydrogen or fluorine,
R4 is hydrogen,
R5 is methyl,
A is ethylene, and the salts, N-oxides and the salts of the N-oxides of these compounds.

Compounds according to embodiment b in more particular worthy to be mentioned are those compounds of formula Ib, in which either
R1 is methyl,
R2 is methyl, and
R3 is fluorine, or
R1 is hydrogen, methyl or ethyl,
R2 is hydrogen, methyl or ethyl, and
R3 is hydrogen,
R4 is hydrogen,
R5 is methyl,
A is ethylene, and the salts, N-oxides and the salts of the N-oxides of these compounds.

A more preferred embodiment (embodiment c) of this invention include compounds of formula Ic in which
R1 is hydrogen or 1-4C-alkyl,
R2 is hydrogen or 1-4C-alkyl,
R3 is hydrogen or halogen,
R4 is hydrogen,
R5 is methyl,
A is ethylene, and the salts, N-oxides and the salts of the N-oxides of these compounds.

Compounds according to embodiment c more worthy to be mentioned are those compounds of formula Ic, in which
R1 is hydrogen, methyl or ethyl,
R2 is hydrogen, methyl or ethyl,
R3 is hydrogen, chlorine or fluorine,
R4 is hydrogen,
R5 is methyl,
A is ethylene, and the salts, N-oxides and the salts of the N-oxides of these compounds.

Compounds according to embodiment c in particular worthy to be mentioned are those compounds of formula Ic, in which either
R1 is hydrogen, methyl or ethyl,
R2 is hydrogen, methyl or ethyl,
R3 is hydrogen or fluorine,
R4 is hydrogen,
R5 is methyl,
A is ethylene, and the salts, N-oxides and the salts of the N-oxides of these compounds.

Compounds according to embodiment c in more particular worthy to be mentioned are those compounds of formula Ic, in which either
R1 is methyl,
R2 is methyl, and
R3 is fluorine, or
R1 is hydrogen, methyl or ethyl,
R2 is hydrogen, methyl or ethyl, and
R3 is hydrogen,
R4 is hydrogen,
R5 is methyl,
A is ethylene, and the salts, N-oxides and the salts of the N-oxides of these compounds.

As exemplary compounds according to this invention the following compounds of formula Id

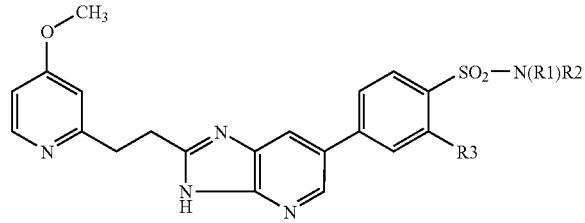

(Id)

are to be mentioned by means of the substituent meanings for R1, R2 and R3 in the following Table 1.

TABLE 1

| R1 | R2 | R3 |
|---|---|---|
| H | H | H |
| H | CH$_3$ | H |
| H | CH$_2$CH$_3$ | H |
| H | H | F |
| H | CH$_3$ | F |
| H | CH$_2$CH$_3$ | F |
| CH$_2$CH$_3$ | CH$_2$CH$_3$ | H |
| CH$_3$ | CH$_3$ | H |
| CH$_3$ | CH$_2$CH$_3$ | H |
| CH$_2$CH$_3$ | CH$_2$CH$_3$ | F |
| CH$_3$ | CH$_3$ | F |
| CH$_3$ | CH$_2$CH$_3$ | F | and the salts, N-oxides and the salts of the N-oxides of these compounds.

Compounds according to this invention can be obtained as described below and shown in the following reaction schemes, or as specified by way of example in the following examples or similarly or analogously thereto.

Thus, as shown in reaction scheme I below, a compound of formula II, in which R4, R5 and A have the meanings given above and X is a suitable leaving group, preferably bromine or, particularly, iodine, is reacted with boronic acids or, particularly, boronic acid esters (e.g. pinacol esters) of formula IIa, in which R1, R2 and R3 have the meanings given above and Y is a boronic acid group or, particularly, a boronic acid ester group, suitably a cyclic boronic acid ester group such as, for example, the boronic acid pinacol ester group, under conditions appropriate for a Suzuki reaction to occur to give compounds of formula I, in which R1, R2, R3, R4, R5 and A have the meanings mentioned above.

Reaction Scheme 1:

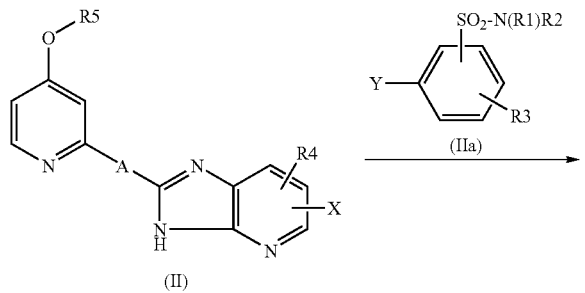

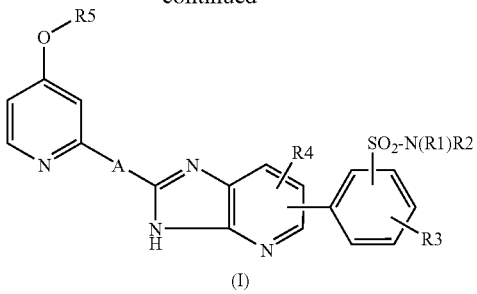

(I)

Suitably, the Suzuki reaction is carried out as it is known to the person of ordinary skill in the art and/or in a manner as it is described below and specified by way of example in the following examples or analogously or similarly thereto.

In more detail, the Suzuki reaction mentioned can be carried out in organic solvents alone, for example in toluene, benzene, dimethylformamide or in ethereal (e.g. dimethoxyethane or, in particular, dioxane) or alcohol solvents or in a mixture thereof, or preferably in a mixture comprising an organic solvent (in particular dioxane) and water, with organic (e.g. triethylamine) or preferably inorganic base (e.g. potassium hydroxide, thallium hydroxide, sodium bicarbonate, cesium carbonate, cesium fluoride or, in particular, potassium carbonate) in the presence of a transition metal catalyst, for example, a nickel or, in particular, palladium catalyst (e.g. Pd(OAc)$_2$, PdCl$_2$(PPh$_3$)$_2$ or, in particular, Pd(PPh$_3$)$_4$), and, optionally, lithium chloride. The reaction is carried out at a temperature in the range from 20° to 160° C., usually 60° to 130° C. for 10 minutes to 5 days, usually 30 minutes to 24 hours. Advantageously, the solvents used are degassed and the reaction is carried out under protective gas.

The Suzuki reaction is for example described in Tetrahedron Lett. 1998, 39, 4467, J. Org. Chem. 1999, 64, 1372 or Heterocycles 1992, 34, 1395. A general review of Suzuki cross-couplings between boronic acids and aryl halides can be found in Miyaura, N; Suzuki, A. Chem. Rev. 1995, 95, 2457.

Boronic acids or boronic acid esters (e.g. pinacol esters) of formula IIa, in which R1, R2, R3 and Y have the meanings given above, are known or can be obtained in an art-known manner or analogously or similarly to known compounds. Boronic acid esters (e.g. pinacol esters) of formula IIa can be prepared, for example, as described in the following examples starting from phenyl triflates or, particularly, phenyl halides, preferably the bromides or iodides, using e.g. bis-(pinacolato)-diboron in the presence of a transition metal, preferably palladium, catalyst Optionally the boronic acid esters obtained can be isolated or, preferably, they are generated in situ and used in the subsequent Suzuki reaction without isolation.

Compounds of formula II, in which R4, R5, X and A have the meanings given above, are obtained as exemplarily described in the following examples or shown in the following reaction scheme 2 or similarly or analogously thereto.

In the following reaction scheme 2 the synthesis of compounds of formula 11, in which R4, R5 and X have the meanings given above and A is ethylene, is exemplarily described.

The carbon chain in 2-position of the compounds of formula VII is lengthened, for example, by a condensation (with a malonic acid derivative) and a subsequent hydrogenation reaction. Alternatively, the carbon chain can be lengthened using a Wittig reaction followed by a hydrogenation reaction.

The methyl 3-(4(1-4C)-alkoxypyridin-2-yl)propionate (compound of formula V) or the corresponding acid (compound of formula IV), which can be obtained in an art-known manner, are converted with a 2,3-diaminopyridine derivative (compound of formula III) to give the desired compounds of formula II.

The synthesis of 3-(4-methoxypyridin-2-yl)propionic acid (compound of formula IV) is described in the paragraph Starting Materials.

Compounds of formula III, in which R4 and X have the meanings indicated above, are known or can be prepared in a known manner or analogously or similarly to art-known compounds.

Reaction Scheme 2:

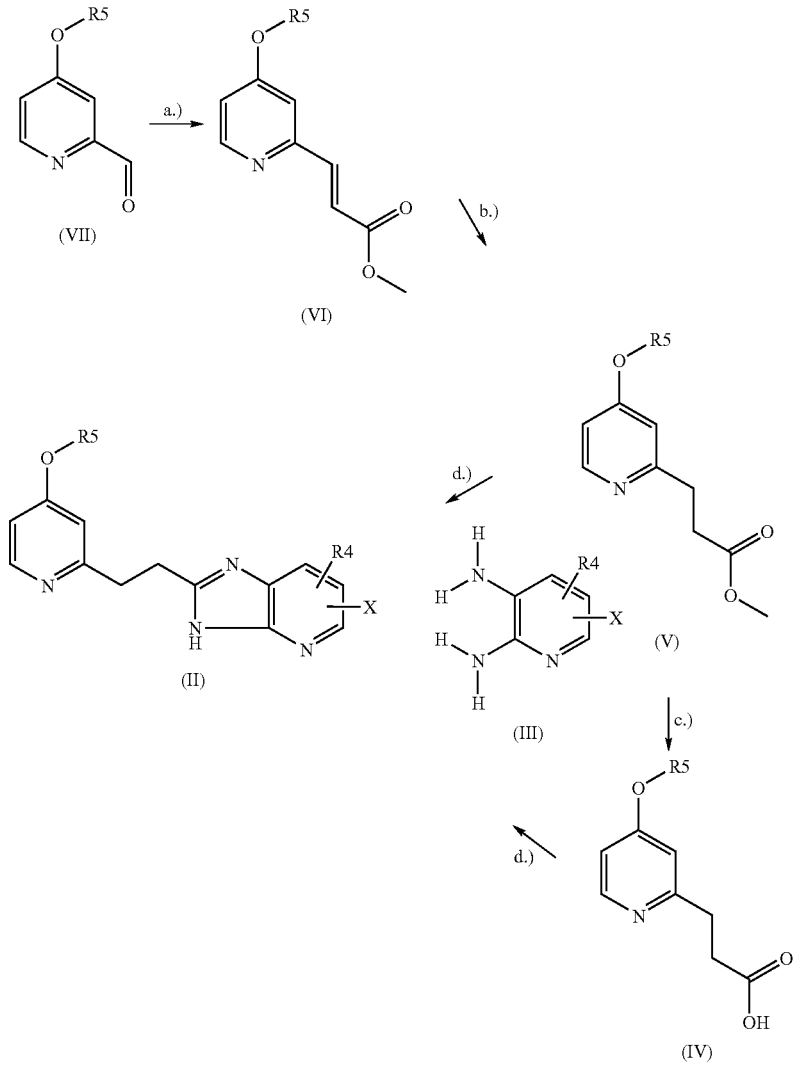

a.) Monomethyl malonate potassium salt/piperidine/pyridine
b.) H₂/Pd/C (10%)
c.) NaOH
d.) Polyphosphoric acid The synthesis of 4-methoxy-pyridin-2-carbaldehyde (compound of formula VII) is described for example in Ashimori et al, Chem Pharm Bull 38, 2446-2458 (1990).

Compounds of formula VII can be also prepared starting from commercially available 4-nitro-2-picoline-N-oxide by exchange of the nitro group by an 1-4C-alkoxy group. The resulting 4-(1-4C)-alkoxy-2-picoline-N-oxide is then via a rearrangement and an oxidation step converted to 4-(1-4C)-alkoxy-pyridin-2-carbaldehyd (compound of formula VII).

Optionally, the compounds according to this invention can be converted into their salts, or, optionally, salts of the compounds according to this invention can be converted into the free compounds. Corresponding processes are known to the person skilled in the art.

The compounds according to this invention can be converted, optionally, into their N-oxides, for example with the aid of hydrogen peroxide in methanol or with the aid of m-chloroperoxybenzoic acid in dichloromethane. The person skilled in the art is familiar on the basis of his/her expert knowledge with the reaction conditions which are specifically necessary for carrying out the N-oxidation.

It is known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1999, $3^{rd}$ Ed, or in P. Kocienski, Protecting Groups, Thieme Medical Publishers, 2000.

The substances according to the invention are isolated and purified in a manner known per se, e.g. by distilling off the solvent in vacuo and recrystallizing the residue obtained from a suitable solvent or subjecting it to one of the customary purification methods, such as column chromatography on a suitable support material.

Salts are obtained by dissolving the free compound in a suitable solvent (for example a ketone like acetone, methylethylketone, or methylisobutylketone, an ether, like diethyl ether, tetrahydrofuran or dioxane, a chlorinated hydrocarbon, such as methylene chloride or chloroform, or a low molecular weight aliphatic alcohol, such as ethanol, isopropanol) which contains the desired acid, or to which the desired acid is then added. The salts are obtained by filtering, reprecipitating, precipitating with a non-solvent for the addition salt or by evaporating the solvent. Salts obtained can be converted by basification into the free compounds which, in turn, can be converted into salts. In this manner, pharmacologically non-tolerable salts can be converted into pharmacologically tolerable salts.

Suitably, the conversions mentioned in this invention can be carried out analogously or similarly to methods which are familiar per se to the person skilled in the art, for example, in the manner which is described by way of example in the following examples.

The person skilled in the art knows on the basis of his/her knowledge and on the basis of those synthesis routes, which are shown and described within the description of this invention, how to find other possible synthesis routes for compounds according to this invention. All these other possible synthesis routes are also part of this invention.

Having described the invention in detail, the scope of the present invention is not limited only to those described characteristics or embodiments. As will be apparent to persons skilled in the art, modifications, analogies, variations, derivations, homologisations and adaptations to the described invention can be made on the base of art-known knowledge and/or, particularly, on the base of the disclosure (e.g. the explicite, implicite or inherent disclosure) of the present invention without departing from the spirit and scope of this invention as defined by the scope of the appended claims.

The following examples illustrate the invention in greater detail, without restricting it. As well, further compounds according to the present invention, of which the preparation is explicitly not described, can be prepared in an analogous way or in a way which is known by a person skilled in the art using customary preparation methods and process techniques.

The compounds, which are mentioned in the examples as well as their salts are a preferred subject of the invention.

In the examples, m.p. stands for melting point, h for hours, d for days, min for minutes, TLC for thin layer chromatography, Rf for retention factor, MS for mass spectrum, M for molecular ion, other abbreviations have their meanings customary per se for the skilled person.

EXAMPLES

Final Products 1. 4-{2-[2-(4-Methoxypyridin-2-yl)ethyl]-3H-imidazo[4,5-b]pyridin-6-yl}-N,N-dimethyl-benzenesulfonamide A mixture of 1.984 g of N,N-dimethyl4-bromobenzenesulfonamide, 2.1 g of bis-(pinacolato)-diboron, 0.125 g of 1,1'-bis-(diphenylphosphino)-ferrocene, 0.165 g of [1,1'-bis(diphenyl-phosphino)ferrocene]palladium-dichloride (complex with $CH_2Cl_2$), 2.21 g of potassium acetate in 50 ml of degassed dioxane are heated to reflux under $N_2$ for 16 hours. To the resulting mixture 40 ml of degassed dioxane, 2.14 g of 2-[2-(4-methoxypyridin-2-yl)ethyl]-6-iodo-3H-imidazo[4,5-b]pyridine (starting material A1), 0.65 g of tetrakis(triphenylphos-phine)-palladium(0) and a solution of 1.56 g of potassium carbonate and 0.48 g of lithium chloride in 40 ml of degassed water are added under $N_2$. The mixture is heated to reflux under $N_2$ for 7 hours and, after cooling, addition of water and adjusting the pH to 7, it is extracted three times with dichloromethane. The combined organic phases are dried over sodium sulfate, concentrated and the residue is chromatographed on a silica gel column (dichloromethane/methanol 30-15:1). Concentration of the chromatographically pure fractions, crystallization from methanol and recrystallization from ethylacetate gives 2.01 g of the title compound as a solid of m.p. 217-218° C. The mass spectrum shows the molecular peak $MH^+$ at 438.3 Da.

2. N,N-Diethyl-4-{2-[2-(4-methoxypyridin-2-yl)ethyl]-3H-imidazo-[4,5-b]pyridin-6-yl}benzenesulfonamide A mixture of 0.438 g of N,N-diethylbromobenzenesulfonamide, 0.42 g of bis-(pinacolato)diboron, 0.025 g of 1,1'-bis-(diphenylphosphino)-ferrocene, 0.033 g of [1,1'-bis(diphenyl-phosphino)ferrocene]palladium-dichloride (complex with $CH_2Cl_2$), 0.442 g of potassium acetate in 6 ml of degassed dioxane are heated to 90° C. in a sealed tube under $N_2$ for 7 hours. To the resulting mixture 10 ml of degassed dioxane, 0.371 g of 2-[2-(4-methoxypyridin-2-yl)ethyl]-6-iodo-3H-imidazo[4,5-b]pyridine (starting material A1), 0.113 g of tetrakis(triphenylphos-phine)-palladium(0) and a solution of 0.27 g of potassium carbonate and 0.083 g of lithium chloride in 10 ml of degassed water are added under $N_2$. The mixture is heated to reflux under $N_2$ for 16 hours and, after cooling, addition of water and adjusting the pH to 7, it is extracted three times with dichloromethane. The combined organic phases are dried over sodium sulfate, concentrated and the residue is chromatographed on a silica gel column (dichloromethane/methanol 30-25:1). Concentration of the chromatographically pure fractions and crystallisation from ethylacetate gives 0.155 g of the title compound as a solid of m.p. 127-129° C. The mass spectrum shows the molecular peak $MH^+$ at 466.3 Da.

3. 4-{2-[2-(4-Methoxypyridin-2-yl)ethyl]-3H-imidazo[4,5-b]pyridin-6-yl}-N-methyl-benzenesulfonamide A mixture of 0.375 g of N-methyl-4-bromobenzenesulfonamide, 0.42 g of bis-(pinacolato)-diboron, 0.025 g of 1,1'-bis-(diphenylphosphino)-ferrocene, 0.033 g of [1,1'-bis(diphenylphosphino)-ferrocene]palladium-dichloride (complex with CH$_2$Cl$_2$), 0.442 g of potassium acetate in 6 ml of degassed dioxane are heated to 90° C. in a sealed tube under N$_2$ for 16 hours. To the resulting mixture 5 ml of degassed dioxane, 0.371 g of 2-[2-(4-methoxypyridin-2-yl)ethyl]-6-iodo-3H-imidazo[4,5-b]pyridine (starting material A1), 0.113 g of tetrakis(triphenylphos-phine)-palladium(0) and a solution of 0.27 g of potassium carbonate and 0.083 g of lithium chloride in 5 ml of degassed water are added under N$_2$. The tube is sealed again, the mixture is heated to 90° under N$_2$ for 8 hours and, after cooling, addition of water and adjusting the pH to 7, it is extracted three times with dichloromethane. The combined organic phases are dried over sodium sulfate, concentrated and the residue is chromatographed on a silica gel column (dichloromethane/methanol 20-15:1). Concentration of the chromatographically pure fractions and crystallisation from ethyacetate gives 0.219 g of the title compound as a solid of m.p. 225-227° C. The mass spectrum shows the molecular peak MH$^+$ at 424.3 Da.

4. 4-{2-[2-(4-Methoxypyridin-2-yl)ethyl]-3H-imidazo[4,5-b]pyridin-6-yl}-benzenesulfonamide A mixture of 0.354 g of 4-bromobenzenesulfonamide, 0.42 g of bis-(pinacolato)-diboron, 0.025 g of 1,1'-bis-(diphenylphosphino)-ferrocene, 0.033 g of [1,1'-bis(diphenylphosphino)ferrocene]-palladium-dichloride (complex with CH$_2$Cl$_2$), 0.442 g of potassium acetate in 6 ml of degassed dioxane are heated to 125° C. in a sealed tube under N$_2$ for 16 hours. To the resulting mixture 5 ml of degassed dioxane, 0.371 g of 2-[2-(4-methoxypyridin-2-yl)ethyl]-6-iodo-3H-imidazo[4,5-b]pyridine (starting material A1), 0.113 g of tetrakis(triphenylphos-phine)palladium(0) and a solution of 0.27 g of potassium carbonate and 0.083 g of lithium chloride in 5 ml of degassed water are added under N$_2$. The tube is sealed again, the mixture is heated to 115° under N2 for 7 hours and, after cooling, addition of water and adjusting the pH to 7, it is extracted three times with dichloromethane. The combined organic phases are dried over sodium sulfate, concentrated and the residue is chromatographed on a silica gel column (dichloromethane/methanol 12:1+1% NH$_4$OH). Concentration of the chromatographically pure fractions gives 0.08 g of the title compound as a brownish solid of m.p. 216-218° C. The mass spectrum shows the molecular peak MH$^+$ at 410.2 Da.

5. N-Ethyl-4-{2-[2-(4-methoxypyridin-2-yl)ethyl]-3H-imidazo-[4,5-b]pyridin-6-yl}benzenesulfonamide A mixture of 0.348 g of N-ethyl4-bromobenzenesulfonamide, 0.42 g of bis-pinacolato)diboron, 0.025 g of 1,1'-bis-(diphenylphosphino)-ferrocene, 0.033 g of [1,1'-bis(diphenylphosphino)-ferrocene]palladium-dichloride (complex with CH$_2$Cl$_2$), 0.442 g of potassium acetate in 6 ml of degassed dioxane are heated to 90° C. in a sealed-tube under N$_2$ for 17 hours. To the resulting mixture 5 ml of degassed dioxane, 0.371 g of 2-[2-(4-methoxypyridin-2-yl)ethyl]-6-iodo-3H-imidazo[4,5-b]pyridine (starting material A1), 0.113 g of tetrakis(triphenylphos-phine)-palladium(0) and a solution of 0.27 g of potassium carbonate and 0.083 g of lithium chloride in 5 ml of degassed water are added under N$_2$. The tube is sealed again, the mixture is heated to 115° under N2 for 7 hours and, after cooling, addition of water and adjusting the pH to 7, it is extracted three times with dichloromethane. The combined organic phases are dried over sodium sulfate, concentrated and the residue is chromatographed on a silica gel column (dichloromethane/methanol 25-15:1). Concentration of the chromatographically pure fractions and crystallisation from ethylacetate gives 0.248 g of the title compound as a solid of m.p. 214-216° C. The mass spectrum shows the molecular peak MH$^+$ at 438.4 Da.

6. 2-Fluoro-4-{2-[2-(4-methoxypyridin-2-yl)ethyl]-3H-imidazo[4,5-b]pyridin-6-yl}-N,N-dimethyl-benzenesulfonamide A mixture of 0.423 9 of N,N-dimethyl4-bromo-2-fluorobenzenesulfonamide, 0.42 g of bis-(pinacolato)-diboron, 0.025 g of 1,1'-bis-(diphenylphosphino)-ferrocene, 0.033 g of [1,1'-bis(diphenylphosphino)-ferrocene]palladium-dichloride (complex with CH$_2$Cl$_2$), 0.442 g of potassium acetate in 6 ml of degassed dioxane are heated to 90° C. in a sealed tube under N$_2$ for 17 hours. To the resulting mixture 5 ml of degassed dioxane, 0.371 g of 2-[2-(4methoxypyridin-2-yl)ethyl]6-iodo-3H-imidazo[4,5-b]pyridine (starting material A1), 0.113 g of tetrakis(triphenylphos-phine)-palladium(0) and a solution of 0.27 g of potassium carbonate and 0.083 g of lithium chloride in 5 ml of degassed water are added under N$_2$. The tube is sealed again, the mixture is heated to 115° under N$_2$ for 7 hours and, after cooling, addition of water and adjusting the pH to 7, it is extracted three times with dichloromethane. The combined organic phases are dried over sodium sulfate, concentrated and the residue is chromatographed on a silica gel column (dichloromethane/methanol 25-22:1). Concentration of the chromatographically pure fractions and crystallisation from ethylacetate gives 0.27 g of the title compound as a solid of m.p. 211-212° C. The mass spectrum shows the molecular peak MH$^+$ at 456.3 Da.

Starting Materials:

A1. 2-[2-(4-Methoxypyridin-2-yl)ethyl]-6-iodo-3H-imidazo[4,5-b]pyridine

With stirring, a mixture of 8.06 g of 3-(4methoxypyridin-2-yl)propionic acid (starting material B1), 9.5 g of 2,3-diamino-5-iodopyridine (Cugola et al., Bioorg. Med. Chem. Lett. 2.2 2749-2754 (1996)) and 150 g of polyphosphoric acid (PPA) is heated at 140° C. for 22 hours. After cooling, the mixture is poured into about 1000 ml of ice-water and then neutralized (pH 78) using 6N aqueous sodium hydroxide solution. The mixture is extracted four times with ethyl acetate and the combined organic phases are evaporated to dryness. The residue is crystallized first from ethyl acetate and then from methanol, giving 9.4 g of the title compound as a light-beige powder of m.p. 207-208° C.; the mass spectrum shows the molecular peak MH$^+$ at 381.2 Da.

B1. 3-(4-Methoxypyridin-2-yl)propionic acid 41.95 g of methyl 3-(4-methoxypyridin-2-yl)propionate (starting material C1) are dissolved in 700 ml of tetrahydrofuran, and 217 ml of 1N sodium hydroxide solution are added. The mixture is stirred at RT until no more starting material is detectable (TLC). The mixture is neutralized using 217 ml of 1N hydrochloric acid solution, evaporated to dryness and dried under high vacuum. The colorless residue is ground and extracted four times with dichloromethane/methanol (9:1). The combined extracts are evaporated to dryness. This gives 33.2 g of the title compound as a colorless powder of m.p. 131-132° C. The mass spectrum shows the molecular peak MH$^+$ at 182 Da.

C1. Methyl 3-(4-methoxypyridin-2-yl)propionate 43.1 g of methyl 3-(4-methoxypyridin-2-yl)acrylate (starting material D1) in 600 ml of methanol are hydrogenated over 3.0 g of Pd/C (10% strength) until the starting material has disappeared (TLC). The catalyst is filtered off, and the mixture is then concentrated and dried under high vacuum. This gives 41.95 g of the title compound as a light-yellow oil. The mass spectrum shows the molecular peak MH$^+$ at 196 Da.

D1. Methyl 3-(4-methoxypyridin-2-yl)acrylate

A mixture of 45 g of 4-methoxypyridin-2-carbaldehyde (Ashimori et al., Chem. Pharm. Bull. 38, 2446-2458 (1990)), 75.80 g of pyridine hydrochloride, 102.45 g of monomethyl malonate potassium salt and 4.1 ml of piperidine in 700 ml of pyridine are slowly heated, with stirring, to 120° C. When the evolution of gas starts, the heating source is temporarily removed to stop the reaction from becoming too violent. Once the reaction has subsided, the mixture is stirred at 120° C. for a further 2.5 hours, and the pyridine is then distilled off under reduced pressure. The residue is partitioned between ethyl acetate/water and the organic phase is washed with water and dried. The residue obtained after concentration is chromatographed on a silica gel column using ethyl acetate/petroleum ether 2:1. This initially gives 43.2 g of the title compound as a yellow oil which crystallizes on standing and then shows a m.p. of 80-82° C. The mass spectrum shows the molecular peak MH$^+$ at 194 Da.

Commercial Applicability

The compounds according to the invention have valuable, desired and emphasis worth pharmacological properties which make them commercially utilizable. They are selective inhibitors of the enzyme inducible nitric oxide synthase. Nitric oxide syntheses (NO-syntases, NOSs) are enzymes that generate NO and citrulline from the amino acid arginine. In certain pathophysiological situations such as arginine depletion or tetrahydrobiopterin depletion the generation of $O_2^-$ from NO-synthases instead or together with NO has been reported. NO is long known as a signaling molecule in most living organisms including mammals and humans. The most prominent action of NO is it's smooth muscle relaxing activity, which is caused on the molecular level by the activation of soluble guanylate cyclase. In the last years a lot of other enzymes have been shown to be regulated by NO or reaction products of NO.

There exist three isoforms of NO-synthases which fall into two classes and differ in their physiologic functions and molecular properties. The first class, known as constitutive NO-synthases, comprises of the endothelial NO-synthase and the neuronal NO-synthase. Both isoenzymes are expressed constitutively in various cell types, but are most prominent in endothelial cells of blood vessel walls (therefore called endothelial NO-synthase, eNOS or NOS-III) and in neuronal cells (therefore called neuronal NO-synthase, nNOS or NOS-I). Activation of these two enzymes is dependent on $Ca^{2+}$/Calmodulin which is generated by transient increases of the intracellular free $Ca^{2+}$ concentration. Activation of constitutive isoforms leads to transient bursts of nitric oxide resulting in nanomolar cellular or tissue NO concentrations. The endothelial isoform is involved in the physiologic regulation of blood pressure. NO generated by the neuronal isoform seems to have neurotransmitter function and the neuronal isoform is among other regulatory processes involved in memory function (long term potentiation).

In contrast to the constitutive isoforms the activation of inducible NO-synthase (iNOS, NOS-II), the sole member of the second class, is performed by transcriptional activation of the iNOS-promoter. Proinflammatory stimuli lead to transcription of the gene for inducible NO-synthase, which is catalytically active without increases in the intracellular $Ca^{2+}$-concentration. Due to the long half live of the inducible NO-synthase and the unregulated activity of the enzyme, high micromolar concentrations of NO are generated over longer time periods. These high NO-concentrations alone or in cooperation with other reactive radicals such as $O_2^-$ are cytotoxic. Therefore, in situations of microbial infections, iNOS is involved in cell killing by macrophages and other immune cells during early nonspecific immune responses.

There are a number of pathophysiological situations which among others are characterized by the high expression of inducible NO-synthase and concomitant high NO or $O_2^-$ concentrations. It has been shown that these high NO concentrations alone or in combination with other radical species lead to tissue and organ damage and are causally involved in these pathophysiologies. As inflammation is characterized by the expression of proinflammatory enzymes, including inducible NO-synthase, acute and chronical inflammatory processes are promising diseases for the therapeutic application of selective inhibitors of inducible NO-synthase. Other pathophysiologies with high NO-production from inducible NO-synthase are several forms of shock (septic, hemorrhagic and cytokine-induced). It is clear that nonselective NO-synthase inhibitors will lead to cardiovascular and neuronal side effects due to concomitant inhibition of constitutive NO-synthase isoforms.

It has been shown in in-vivo animal models of septic shock that reduction of circulating plasma NO-levels by NO-scavenger or inhibition of inducible NO-synthase restores systemic blood pressure, reduces organ damage and increases survival (deAngelo Exp. Opin. Pharmacother. 19-29, 1999; Redl et al. Shock 8, Suppl. 51, 1997; Strand et al. Crit. Care Med. 26, 1490-1499, 1998). It has also been shown that increased NO production during septic shock contributes to cardiac depression and myocardial dysfunction (Sun et al. J. Mol. Cell Cardiol. 30, 989-997, 1998). Furthermore there are also reports showing reduced infarct size after occlusion of the left anterior coronary artery in the presence of NO-synthase inhibitors (Wang et al. Am. J. Hyperttens. 12,174-182, i999). Considerable inducible NO-synthase activity is found in human cardiomyopathy and myocarditis, supporting the hypothesis that NO accounts at least in part for the dilatation and impaired contractility in these pathophysiologies (de Belder et al. Br. Heart. J. 4, 426-430,1995).

In animal models of acute or chronic inflammation, blockade of inducible NO-synthase by isoform-selective or nonselective inhibitors or genetic knock out improves therapeutic outcome. It is reported that experimental arthritis (Connor et al. Eur. J. Pharmacol. 273, 15-24, 1995) and osteoarthritis (Pelletier et al. Arthritis & Rheum. 41, 1275-1286, 1998), experimental inflammations of the gastro-intestinal tract (Zingarelli et al. Gut 45, 199-209, 1999), experimental glomerulonephritis (Narita et al. Lab. Invest. 72, 17-24, 1995), experimental diabetes (Corbett et al. PNAS 90, 8992-8995, 1993), LPS-induced experimental lung injury is reduced by inhibition of inducible NO-synthase or in iNOS-knock out mice (Kristof et al. Am. J. Crit. Care. Med. 158, 1883-1889, 1998). A pathophysiological role of inducible NO-synthase derived NO or $O_2^-$ is also discussed in chronic inflammatory diseases such as asthma, bronchitis and COPD.

Furthermore, in models of neurodegenerative diseases of the CNS such as MPTP-induced parkinsonism, amyloid peptide induced Alzheimer's disease (Ishii et al., FASEB J. 14, 1485-1489, 2000), malonate induced Huntington's disease (Connop et al. Neuropharmacol. 35,459-465, 1996), experimental menengitis (Korytko & Boje Neuropharmacol. 35, 231-237, 1996) and experimental encephalitis (Parkinson et al. J. Mol. Med. 75, 174-186,1997) a causal participation of NO and inducible NO-synthase has been shown.

Increased iNOS expression has been found in the brains of AIDS victims and it is reasonable to assume a role of iNOS in AIDS related dementia (Bagasra et al. J. Neurovirol. 3 153-167, 1997).

Other studies implicated nitric oxide as a potential mediator of microglia dependent primary demyelination, a hallmark of multiple sklerosis (Parkinson et al. J. Mol. Med. 75, 174-186, 1997).

An inflammatory reaction with concomitant expression of inducible NO-synthase also takes place during cerebral ischemia and reperfusion (Iadecola et al. Stroke 27, 1373-1380, 1996). Resulting NO together with $O_2^-$ from infiltrating neutrophils is thought to be responsible for cellular and organ damage.

Also, in models of traumatic brain injury (Mesenge et al. J. Neurotrauma 13, 209-214, 1996; Wada et al. Neurosurgery 43, 1427-1436, 1998) NO-synthase inhibitors have been show to posses protective properties. A regulatory role for inducible NO-synthase has been reported in various tumor cell lines (Tozer & Everett Clin Oncol. 9. 357-264, 1997).

On account of their inducible NO-synthase-inhibiting properties, the compounds according to the invention can be employed in human and veterinary medicine and therapeutics, where an excess of NO or $O_2^-$ due to increases in the activity of inducible NO-synthase is involved. They can be used without limitation for the treatment and prophylaxis of the following diseases:

Acute inflammatory diseases: Septic shock, sepsis, SIRS, hemorrhagic shock, shock states induced by cytokine therapy (IL-2, TNF), organ transplantation and transplant rejection, head trauma, acute lung injury, ARDS, inflammatory skin conditions such as sunburn, inflammatory eye conditions such as uveitis, glaucoma and conjunctivitis.

Chronic inflammatory diseases of peripheral organs and the CNS: gastrointestinal inflammatory diseases such as Crohn's disease, inflammatory bowel disease, ulcerative colitis, lung inflammatory diseases such as asthma and COPD, arthritic disorders such as rheumatoid arthritis, osteoarthritis and gouty arthritis, heart disorders such as cardiomyopathy and myocarditis, artherosklerosis, neurogenic inflammation, skin diseases such as psoriasis, dermatitis and eczema, diabetes, glomerulonephritis; dementias such as dementias of the Alzheimer's type, vascular dementia, dementia due to a general medical condition, such as AIDS-, Parkinson's disease, Huntington's induced dementias, ALS, multiple sklerosis; necrotizing vasculitides such as polyarteritis nodosa, serum sickness, Wegener's granulomatosis, Kawasaki's syndrom; headaches such as migraine, chronic tension headaches, cluster and vascular headaches, post-traumatic stress disorders; pain disorders such as neuropathic pain; myocardial and cerebral ischemia/reperfusion injury.

The compounds may also be useful in the treatment of cancers that express nitric oxide synthase.

The invention further relates to a method for the treatment of mammals, including humans, which are suffering from one of the abovementioned illnesses. The method is characterized in that a therapeutically active and pharmacologically effective and tolerable amount of one or more of the compounds according to the invention is administered to the ill mammal.

The invention further relates to the compounds according to the invention for use in the treatment and/or prophylaxis of illnesses, especially the illnesses mentioned.

The invention also relates to the use of the compounds according to the invention for the production of pharmaceutical compositions which are employed for the treatment and/or prophylaxis of the illnesses mentioned.

The invention also relates to the use of the compounds according to the invention for the production of pharmaceutical compositions having an iNOS inhibitory activity.

The invention furthermore relates to pharmaceutical compositions for the treatment and/or prophylaxis of the illnesses mentioned, which contain one or more of the compounds according to the invention.

The invention moreover relates to pharmaceutical compositions according to this invention having an iNOS inhibitory activity.

The pharmaceutical compositions are prepared by processes which are known per se and familiar to the person skilled in the art. As pharmaceutical compositions, the compounds according to the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries or excipients which are suitable for the desired pharmaceutical formulations on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

The administration of the pharmaceutical compositions according to the invention may be performed in any of the generally accepted modes of administration available in the art. Illustrative examples of suitable modes of administration include intravenous, oral, nasal, parenteral, topical, transdermal and rectal delivery. Oral and intravenous delivery are preferred.

For the treatment of disorders of the respiratory tract, the compounds according to the invention are preferably also administered by inhalation in the form of an aerosol; the aerosol particles of solid, liquid or mixed composition preferably having a diameter of 0.5 to 10 µm, advantagously of 2 to 6 µm.

Aerosol generation can be carried out, for example, by pressure-driven jet atomizers or ultrasonic atomizers, but advantageously by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

For the treatment of dermatoses, the compounds according to the invention are in particular administered in the form of those pharmaceutical compositions which are suitable for topical application. For the production of the pharmaceutical compositions, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the active compounds is carried out in the order of magnitude customary for iNOS inhibitors. Topical application forms (such as ointments) for the treatment of dermatoses thus contain the active compounds in a concentration of, for example, 0.1-99%. The dose for administration by inhalation is customarily between 0.1 and 10 mg per day. The customary dose in the case of systemic therapy (p.o.) is between 0.3 and 30 mg/kg per day, (i. v.) is between 0.3 and 30 mg/kg/h.

Biological Investigations

Measurement of Inducible NO-Synthase Activity

The assay is performed in 96-well microtiter F-plates (Greiner, Frickenhausen, FRG) in a total volume of 100 µl in the presence of 100 nM calmodulin, 226 µM $CaCl_2$, 477 µM $MgCl_2$, 5 µM flavin-adenine-dinucleotide (FAD), 5 µM flavin mononucleotide (FMN), 0.1 mM NADPH, 7 mM glutathione, 10 µM BH4 and 100 mM HEPES pH 7.2. Arginine concentrations are 0.1 µM for enzyme inhibition experiments. 150000 dpm of [$^3$H]arginine are added to the assay mixture. Enzyme reaction is started by the addition of 4 µg of a crude cytosolic fraction containing human inducible NO-synthase and the reaction mixture is incubated for 45 to 60 min at 37° C. Enzyme reaction is stopped by adding 10 µl of 2M MES-buffer pH 5,0. 50 µl of the incubation mixture are transferred into a MADP N65 filtration microtiter plate (Millipore, Eschborn, FRG) containing already 50 µl of AG-50W-X8 cation exchange resin (Biorad, München, FRG). The resin in the Na loaded form is preequilibrated in water and 70 µl (corresponding to 50 µl dry beads) are pipetted under heavy stirring with a 8 channel pipette into the filtration plate. After pipetting 50 µl of the enzyme reaction mixture onto the filtration plates, the plates are placed on a filtration manifold (Porvair, Shepperton, UK) and the flow through is collected in Pico scintillation plates (Packard, Meriden, Conn.). The resin in the filtration plates is washed with 75 µl of water (1×50 µl and 1×25 µl) which is also collected in the same plate as the sample. The total flow through of 125 µl is mixed with 175 µl of Microscint-40 scintillation cocktail (Packard) and the scintillation plate is sealed with TopSeal P-foil (Packard). Scintillation plates are counted in a szintillation counter.

For the measurement of inducible NO-synthase-inhibiting potencies of compounds increasing concentrations of inhibitors were included into the incubation mixture. $IC_{50}$-values were calculated from the percent inhibition at given concentrations by nonlinear least square fitting.

The inhibitory values determined for the compounds according to the invention follow from the following table A, in which the compound numbers correspond to the example numbers.

TABLE A

Inhibition of iNOS activity [measured as $-logIC_{50}$ (mol/l)]

| compound | $-logIC_{50}$ |
|---|---|
| 1 | 7.83 |
| 2 | 7.45 |
| 3 | 7.86 |
| 4 | 7.83 |
| 5 | 7.62 |
| 6 | 7.67 |

The invention claimed is:

1. A compound of formula I

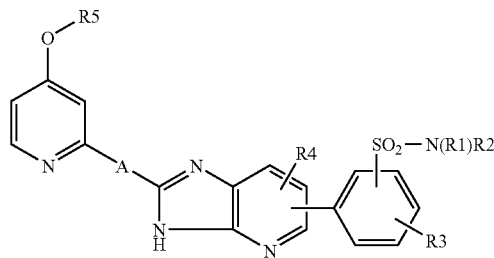

in which
R1 is hydrogen or 1-4C-alkyl,
R2 is hydrogen or 1-4C-alkyl,
R3 is hydrogen or halogen,
R4 is hydrogen, halogen, 1-4C-alkyl or 1-4C-alkoxy,
R5 is 1-4C-alkyl,
A is 1-4C-alkylene,
or a salt, N-oxide or a salt of an N-oxide thereof.

2. The compound of claim 1, wherein said compound has one of the formulae Ia, Ib or Ic:

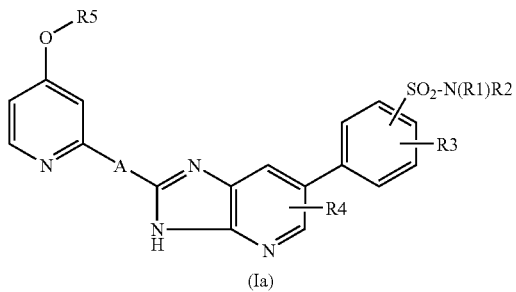

(Ia)

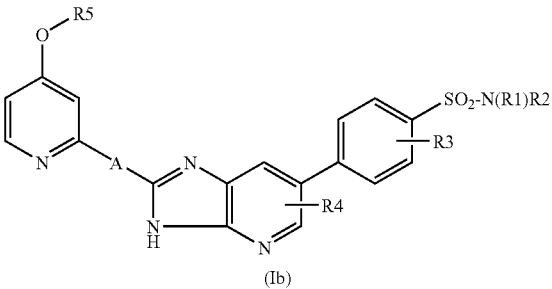

(Ib)

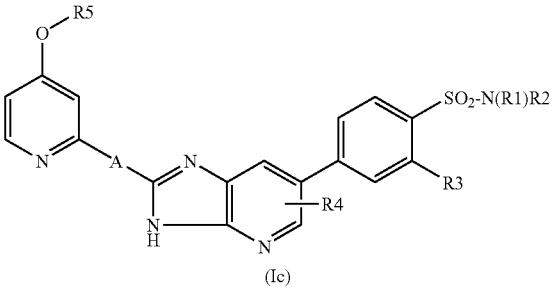

(Ic)

or a salt, N-oxide or a salt of an N-oxide thereof.

3. The compound of claim 1, wherein said compound has one of the formulae I, Ia, Ib or Ic
in which
R1 is hydrogen or 1-4C-alkyl,
R2 is hydrogen or 1-40-alkyl,
R3 is hydrogen or halogen, R4 is hydrogen,
R5 is methyl,
A is ethylene,
or a salt, N-oxide or a salt of an N-oxide thereof.

4. The compound of claim 1, wherein said compound has one of the formulae I, I*a*, I*b* or I*c*
in which
R1 is hydrogen, methyl or ethyl,
R2 is hydrogen, methyl or ethyl,
R3 is hydrogen or fluorine,
R4 is hydrogen,
R5 is methyl,
A is ethylene,
or a salt, N-oxide or a salt of an N-oxide thereof.

5. The compound of claim 1, wherein said compound has one of the formulae I, I*a*, I*b* or I*c*
in which
either
R1 is methyl,
R2 is methyl, and
R3 is fluorine,
or
R1 is hydrogen, methyl or ethyl,
R2 is hydrogen, methyl or ethyl, and
R3 is hydrogen,
R4 is hydrogen,
R5 is methyl,
A is ethylene,
or a salt, N-oxide or a salt of an N-oxide thereof.

6. The compound of claim 1, wherein said compound has one of the formulae I*b* or I*c*
in which
R1 is hydrogen, methyl or ethyl,
R2 is hydrogen, methyl or ethyl,
R3 is hydrogen or fluorine,
R4 is hydrogen,
R5 is methyl,
A is ethylene,
or a salt, N-oxide or a salt of an N-oxide thereof.

7. The compound of claim 1, wherein said compound has the formula I*c*
in which
either
R1 is methyl,
R2 is methyl, and
R3 is fluorine,
or
R1 is hydrogen, methyl or ethyl,
R2 is hydrogen, methyl or ethyl, and
R3 is hydrogen,
R4 is hydrogen,
R5 is methyl,
A is ethylene,
or a salt, N-oxide or a salt of an N-oxide thereof.

8. The compound of claim 1, wherein said compound has the formula Id

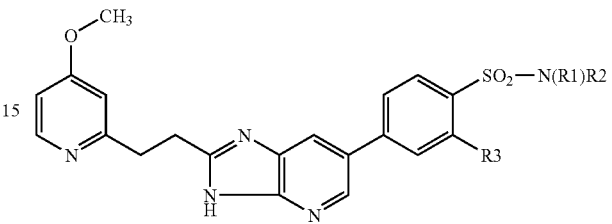

in which R1, R2 and R3 have any one of the following meanings 1 to 12:

|  | R1 | R2 | R3 |
|---|---|---|---|
| 1. | H | H | H |
| 2. | H | $CH_3$ | H |
| 3. | H | $CH_2CH_3$ | H |
| 4. | H | H | F |
| 5. | H | $CH_3$ | F |
| 6. | H | $CH_2CH_3$ | F |
| 7. | $CH_2CH_3$ | $CH_2CH_3$ | H |
| 8. | $CH_3$ | $CH_3$ | H |
| 9. | $CH_3$ | $CH_2CH_3$ | H |
| 10. | $CH_2CH_3$ | $CH_2CH_3$ | F |
| 11. | $CH_3$ | $CH_3$ | F |
| 12. | $CH_3$ | $CH_2CH_3$ | F | or a salt, N-oxide or a salt of an N-oxide thereof.

9. A pharmaceutical composition containing one or more compounds of formula I according to claim 1, or a pharmaceutically acceptable salt, N-oxide or a salt of an N-oxide thereof, together with a pharmaceutically suitable auxiliary and/or excipient.

* * * * *

UNITED STATES PATENT AND TRADEMARK OFFICE
CERTIFICATE OF CORRECTION

PATENT NO. : 7,468,377 B2 Page 1 of 1
APPLICATION NO. : 10/573484
DATED : December 23, 2008
INVENTOR(S) : Wolf-Ruediger Ulrich It is certified that error appears in the above-identified patent and that said Letters Patent is hereby corrected as shown below:

Claim 3, Column 20, Line 66,

Please delete "R2 is hydrogen or 1-40-alkyl,"

and replace with

-- R2 is hydrogen or 1-4C-alkyl, --

Signed and Sealed this

Twenty-fourth Day of March, 2009

JOHN DOLL
*Acting Director of the United States Patent and Trademark Office*